United States Patent [19]

Wurtman

[11] Patent Number: 4,927,853
[45] Date of Patent: May 22, 1990

[54] COMPOSITION FOR INCREASING BLOOD PRESSURE

[75] Inventor: Richard J. Wurtman, Boston, Mass.

[73] Assignee: Massachusetts Institute of Technology, Cambridge, Mass.

[21] Appl. No.: 156,109

[22] Filed: Feb. 16, 1988

Related U.S. Application Data

[60] Division of Ser. No. 665,579, Oct. 29, 1984, Pat. No. 4,745,130, which is a continuation of Ser. No. 366,887, Apr. 8, 1982, abandoned, which is a continuation-in-part of Ser. No. 88,226, Oct. 25, 1979, abandoned, which is a continuation of Ser. No. 898,740, Apr. 27, 1978, abandoned.

[51] Int. Cl.$^5$ .............................................. A61K 31/05
[52] U.S. Cl. .................................................... 514/567
[58] Field of Search ......................................... 514/567

[56] References Cited

U.S. PATENT DOCUMENTS

| | | | |
|---|---|---|---|
| 3,896,166 | 7/1975 | Kaiser et al. | 514/910 |
| 4,053,651 | 10/1977 | Ondetti et al. | 548/336 |
| 4,065,572 | 12/1977 | Atkinson et al. | 514/362 |

OTHER PUBLICATIONS

Chemical Abstracts, vol. 82, Abstract No. 26,037k, 1975.
Chemical Abstracts, vol. 75, Abstract No. 62,013p, 1971.

*Primary Examiner*—Richard A. Schwartz
*Assistant Examiner*—Zinna Northington-Davis
*Attorney, Agent, or Firm*—Paul J. Cook

[57] ABSTRACT

Blood pressure is increased in a patient having a condition which effects rapid fixing of neurons in the sympathetic nervous system and low blood pressure by administering a mixture of (a) (1) phenylalanine or (2) a mixture of phenylalanine and tyrosine and (b) a drug which increases noradrenergic neurotransmission in the sympathetic nervous system.

3 Claims, No Drawings

COMPOSITION FOR INCREASING BLOOD PRESSURE

The Government has rights in this invention pursuant to Grant No. AM-14228 awarded by the National Institute of Health.

REFERENCE TO RELATED APPLICATION

This is a divisional of co-pending application Ser. No. 665,579 filed on 10/29/84 which is a continuation of 366,887 filed Apr. 8, 1982 which is a continuation-in-part of application Ser. No. 088,226, filed Oct. 10, 25, 1979, which in turn is a continuation of Ser. No. 898,740, filed Apr. 27, 1978, now abandoned.

BACKGROUND OF THE INVENTION

This invention relates to a method and composition for increasing blood pressure in a patient having low blood pressure.

It is well known that the neurotransmitter norepinephrine is derived from dihydroxyphenylalanine (DOPA). DOPA is, in turn, produced in neurons by the enzymatic hydroxylation of the amino acid tyrosine. This process is catalyzed by the enzyme tyrosine hydroxylase. The DOPA is decarboxylated to dopamine by the enzyme aromatic L-amino acid decarboxylase (AAAD) and norepinephrine is produced from dopamine in neurons that also contain this reaction chain, the rate-limiting step is the conversion of tyrosine to DOPA. Drugs that act by increasing norepinephrine levels in synapses include the Monoamine Oxidase Inhibitors (which slow the destruction of these neurotransmitters) and the tricyclic antidepressants; these compounds, which are used in treating diseases like depression; also relatively non-specific-producing many chemical effects besides increasing synaptic norepinephrine levels-and thus have a range of unwanted side effects such as the dangerous increases in blood pressure that occur when people receiving monoamine oxidase inhibitors eat certain foods.

Other diseases appear to be caused by the presence of excessive quantities of norepinephrine within synapses including hypertension and cardiac arrhythmias (too much norepinephrine released from sympathetic neurons). These diseases now usually are treated by drugs that block the interactions of norepinephrine with their post-synaptic receptors. However, these agents all exhibit some non-specific actions as well, and thus cause side-effects.

Prior attempts to increase or decrease the levels of dopamine or norepinephrine by modifying neuronal tyrosine levels had been deemed unsuccessful because the total amounts of these compounds in brains and tissues were not noted to change. It was first observed in Wurtman et al (Science 185:183–184, July 12, 1974) that increases in brain DOPA concentrations, which, under the conditions of the experiments varied in proportion to the rates at which dopamine and norepinephrine were being synthesized could be obtained by increasing brain tyrosine concentrations, and that decreases in brain DOPA concentrations could be produced by giving rats treatments that decreased brain tyrosine. An example of a treatment that increased brain tyrosine was the administration of tyrosine itself; an example of a treatment that decreased brain tyrosine was the administration of one of the other neutral amino acids, e.g., leucine, that competes with plasma tyrosine for uptake into the brain. Prior to that disclosure, it had been believed that the rate-limiting enzyme, tyrosine hydroxylase, was so saturated with tyrosine, that increases or decreases in brain tyrosine levels would not affect tyrosine's conversion to DOPA. In neither the above Wurtman et al article nor a subsequent paper by Gibson and Wurtman (Biochem. Pharmacology, 26:1137–1142, June, 1977) was it actually shown that such changes in DOPA accumulation were accompanied by changes in brain dopamine nor norepinephrine levels. Furthermore, in neither was it shown that changing brain tyrosine levels had any effect on the amounts of dopamine nor norepinephrine released into synapses.

It has been disclosed by Laborit et al in Agressologie 1969, Vol. 10, No. 3, pp. 199–215 that animals can be treated for hemorrhagic shock with the combination of tyrosine, chloropromazine and a compound having an SH group or a combination of tyrosine and chloropromazine in order to reduce fatalities. The results set forth in this article also are disclosed in U.S. Pat. No. 3,651,237, issued Mar. 21, 1977. There is no disclosure in these references wherein the person skilled in the art would relate the administration of tyrosine to cause an increase in blood pressure, inasmuch as (a) no data were provided on blood pressures, and, (b) the authors stated that the "... arterial hypotension ... is insensitive to the therapy described." The inventor named in U.S. Pat. No. 3,651,237 has reported in Aggressologie, 1970, Vol. 11, No. 2, pp 139 to 151, and in Aggressologie, 1969, No. 3, pp 241 to 248 that the administration of tyrosine causes a reduction in blood pressure (after stimulation of the vagus nerve). We believe that it would be a mistake to use chlorpromazine along with tyrosine in situations where it is desired to increase blood pressure, inasmuch as this drug blocks certain catecholamine receptors, and can itself lower blood pressure.

It would be highly desirable to provide a means for increasing the amounts of norepinephrine that actually are present within synapses. Such changes in synaptic transmitter levels need not be associated with changes in the total amounts of norepinephrine present in the brain or other tissues, inasmuch as it is now well known that not all of the molecules of the transmitters that are stored in neurons are equally accessible for release into synapses. More specifically, it would be desirable to provide a means for increasing release of norepinephrine in sympathetic neuronal synapses in order to treat conditions to a disease associated with dangerously low blood pressure.

SUMMARY OF THE INVENTION

The present invention provides a method and composition for treating low blood pressure in a patient having a condition characterized by neurons in the sympathetic nervous system that are firing rapidly but are releasing inadequate amounts of norepinephrine. This invention is based upon the discovery that treatments that increase neuronal tyrosine levels can also cause corresponding increases in the amounts of norepinephrine released into synapses. The tyrosine (or its precursor, phenylalanine) can be administered alone or in admixture with other neutral amino acids with or without drugs, in order to raise tyrosine levels in sympathetic neurons; and thereby to treat low blood pressure associated with deficiency of norepinephrine release by these neurons.

DETAILED DESCRIPTION OF SPECIFIC EMBODIMENTS

In accordance with this invention, tyrosine (or phenylalanine) is administered to a patient either alone or in combination with one or more drugs which cause an increase in blood pressure thereby to increase the level of norepinephrine which is released into sympathetic neuronal synapses. (Serotonin release into brain synapses also can be controlled at the same time by varying the proportion of tryptophan present in the amino acid mixture.)

The condition of low blood pressure treated in accordance with this invention can arise from any one of a number of causes including sympathetic neuron malfunction such as orthostatic hypotension or conditions wherein the sympathetic nerves are functioning but are unable to release norepinephrine in sympathetic neuron synapses such as in cases of hemorrhaging, myocardial infarction, septicemia or shock.

The composition of the amino acid mixture that is utilized depends upon the nature of the illness in the patient that is to be treated. When there is need to increase norepinephrine release in sympathetic neuronal synapses without increasing that of brain serotonin, tyrosine (and/or phenylalanine) is administered, with or without other amino acids not including serotonin's precursor, tryptophan, in doses ranging between 5 mg/kg and 200 mg/kg. In some situations, phenylalanine can be used as a substitute for tyrosine, inasmuch as much of this amino acid is converted to tyrosine in the liver.

The amount of tyrosine or phenylalanine administered is between about 2 and 200 mg/kg body weight/day preferably between about 10 and 100 mg/kg body weight/day in order to obtain tyrosine or phenylalanine blood plasma concentrations between about 15 and 100 micrograms/ml, preferably between about 20 and 40 micrograms/ml, thereby to obtain effective increases in blood pressure. When the amino acid is administered in a liquid carrier such as saline or sugar solution, the concentration of tyrosine or phenylalanine should be between about 5 mg/ml and 100 mg/ml. The tyrosine can be administered orally, parenterally or enterally.

The tyrosine, phenylalanine or tryptophan can be administered as free amino acids, esters, salts, natural or synthetic polymers, or as constituents of foods. The route of administration can be oral or parenteral, e.g., intravenous. Tyrosine and/or phenylalanine also can be administered alone or with a drug known to increase blood pressure including neosynephrine, calcium chloride, ephedrine, dopamine or norepinephrine.

The following example illustrates the present invention and is not intended to limit the same.

EXAMPLE I

This example illustrates that an animal having low blood pressure induced by hemorrhaging the animal can have its blood pressure increased into the normal range by administering tyrosine to the animal.

Male Sprague-Dawley rats (Charles River Breeding Laboratories, Wilmington, MA) weighing 350-450 g were housed individually, given ad libitum access to tap water and a stock diet, and maintained under light (300 microwatts/cm$^2$; Vita-Lite, Duro-Test Corp., North Bergen, NJ) between 7 AM and 7 PM daily.

Tyrosine (methyl ester) was dissolved in saline and buffered to pH 7.4 with sodium hydroxide.

A group of 12 rats were hemorrhaged, via the carotid artery, to reduce their calculated blood volume by 15%; blood pressure was reduced by 30±5 mm mercury. After about 15 minutes, the animals then were administered intravascularly either about 0.2 ml saline or about 0.2 of a tryosine solution in saline comprising 100 mg tyrosine/ml saline. The tyrosine dosage corresponded to 100 mg/kg animal body weight. The effects of saline and of tyrosine on blood pressure, 5, 15 or 25 minutes following administration, is shown in Table I.

TABLE I

| Treatment | Time (minutes) | | |
|---|---|---|---|
| | 5 | 15 | 25 |
| | (Rise in Blood Pressure - mm Hg) | | |
| saline | 18 ± 10 | 10 ± 7 | 11 ± 7 |
| Tyrosine | 62 ± 20 | 64 ± 24 | 38 ± 15 |

As shown in Table I tyrosine, but not saline, not only restores blood pressure but actually raises it above normal.

In order to determine whether tyrosine can prevent the development of hemorrhage-induced low blood pressure, groups of 4 rats were intravascularly administered 100 mg/kg body weight tyrosine (100 mg/ml, in saline) comparable volume of saline alone. Five minutes after the tyrosine administration both groups of rats were bled by 10%, 15% or 20% of their total blood volume. Systolic.glood pressures in the animals given saline fell 30±5 mm Hg, 30±7 mm Hg or 50±10 mm Hg, respectively. Systolic glood pressures in animals given the tyrosine fell by only 18±5 mm Hg, 17±4 mm Hg or 29±8 mm Hg, respectively. Hence, tyrosine has utility in the treatment and the prophylaxis of hemorrhage-induced low blood pressure.

What is claimed is:

1. A composition for increasing blood pressure comprising a mixture of (a) a composition selected from the group consisting of (1) phenylalanine and (2) a mixture of phenylalanine and tyrosine and (b) a blood pressure increasing agent selected form the group consisting of neosynephrine, calcium chloride, ephedrine, dopamine and norepinephrine in an amount effective to increase blood pressure wherein the dosage of said composition (a) is between about 5 and 200 mg/kg body weight.

2. The composition of claim 1 wherein composition (a) is phenylalanine.

3. The composition of claim 1 wherein composition (a) is a mixture of phenylalanine and tyrosine.

* * * * *